United States Patent [19]

Ulanovsky

[11] Patent Number: 5,627,032
[45] Date of Patent: May 6, 1997

[54] COMPOSITE PRIMERS FOR NUCLEIC ACIDS

[76] Inventor: Levy Ulanovsky, c/o Dr. Margit Burmeister 3544 Chatham Way, Ann Arbor, Mich. 48105-2828

[21] Appl. No.: 384,699

[22] Filed: Feb. 6, 1995

Related U.S. Application Data

[63] Continuation of Ser. No. 810,898, Dec. 20, 1991, abandoned.

[30] Foreign Application Priority Data

Dec. 24, 1990 [IL] Israel .................................. 098775

[51] Int. Cl.$^6$ .......................... C12Q 1/68; C07H 21/02; C07H 21/04
[52] U.S. Cl. .................... 435/6; 536/23.1; 536/24.3
[58] Field of Search ................ 435/6, 91.2; 536/24.33

[56] References Cited

U.S. PATENT DOCUMENTS 5,114,839  5/1992  Blöcker ........................... 435/6

OTHER PUBLICATIONS

Titeeva et al. Complexing of Single-Stranded Phage DNA with Synthetic Oligodeoxynucleotides . . . Biorgan. Khim. (1986) 12:1484–1491. (translation).
Matthews, J.A. et al. Review: Analytical Strategies for the Use of DNA Probes. Anal. Biochem. (1988) 169: 1–25.
W. Studier, Proc. Natl. Acad. Sci. USA 86, 6917–6921 (1989).
W. Szybalski, Gene 90, 177–178 (1990).
A. Cohen et. al., J. of Chromatography 516, 49–60 (1990).
L. Ulanovsky, G, Drouin and W. Gilbert, Nature 343, 190–192 (1990).
L. Ulanovsky and E. Trifonov, Nature 326, 720–722 (1987).
L. Ulanovsky et al. Proc. Natl. Acad. Sci. USA 83, 862–866 (1986).
LeBoeuf, et al. Cloning and Sequencing of Immunoglobulin Variable–Genes Using Degenerate Oligodeoxyribonucleotides . . . Gene (1989) 82: 371–377.
Watson, et al. Molecular Biology of the Gene (1988) pp. 246–248.
Lu, et al. DNase I Cleavage of Branched DNA Molecules. J. Biol. Chem (1989) 264: 20851–20854.
Nevinsky, G. A., et al. Structure–Function Analysis of Mononucleotides and Short Oligonucleitides in the Priming . . . (Biochemistry (1990) 29:1200–1207).
Kotler, L.E. et al. DNA Sequencing: Modular Primers Assembled from a Library of Hexamers or Pentamers (Proc. Natl. Acad. Sci. USA (May 1993) 90: 4241–4245.

*Primary Examiner*—Stephanie W. Zitomer
*Assistant Examiner*—Ethan Whisenant
*Attorney, Agent, or Firm*—James Remenick; Baker & Botts, L.L.P.

[57] ABSTRACT

A composite nucleic acid primer for a reaction of an enzymatic extension of primer on a template strand; which composite primer comprises two or more covalently unconnected oligonucleotides. Each of the oligonucleotides comprises a binding segment complementary to a binding site in the template strand. The binding segment and the binding site are selected to bind the oligonucleotide to the template strand by means of annealing between the binding segment and the binding site. The binding sites for different oligonucleotides are selected close enough in the template strand to enhance the sequence specificity of priming by the composite primer, as compared to the sequence specificity of priming by one of the oligonucleotides alone. Each of the two oligonucleotides has a segment, preferably 5 to 6 bases long, binding to the template strand. The total primer-to-template annealing length being 10 to 12 bases, the priming site is sufficiently unique in a plasmid size template. An oligonucleotide library (collection) containing an appreciable portion of all possible sequences of a 5-mer segment can be as small as a few hundred samples. The composite primer libraries have fewer samples than a library of similarly unique non-composite primers by about two orders of magnitude, being thus more affordable to users.

13 Claims, 2 Drawing Sheets

COMPOSITE PRIMERS FOR NUCLEIC ACIDS

This application is a continuation of application Ser. No. 07/810,898, filed Dec. 20, 1991, abandoned.

FIELD OF INVENTION

This invention relates to the field of molecular biology of nucleic acids, and specifically to nucleic acid primers and probes. It is of particular interest in terms of its applications to DNA and RNA sequencing.

BACKGROUND

The rate of world wide DNA sequencing is about 50 million bp (base-pairs) a year, doubling approximately every 18 months. With both molecular biology and genetic engineering becoming information oriented, the need for more sequencing information exceeds by far the technical possibility to obtain this information.

At present, a major technique of DNA sequencing in the world is the "walking primer" method used in the framework of the enzymatic sequencing by incorporation of dideoxy chain terminators. In this method the enzymatic sequencing is used to determine the sequence of a few hundred bases of the strand enzymatically extended by a DNA polymerase enzyme in the 5' to 3' direction from a primer, which has primed the extension reaction. This sequencing information is then used to synthesize a new primer to prime the next sequencing reaction further in the 5' to 3' direction of the enzymatically extended strand, and so on. A major advantage of the walking primer method is that it uses the same template for a number of sequencing reactions, thus minimizing the need for subcloning and for other steps in template preparation. Another advantage of the walking primer method is that it facilitates integration of sequences obtained from individual runs into continuous contigs of sequence. A major disadvantage of the walking primer method is the high cost of synthesis of a new primer for each sequencing reaction. Another disadvantage is the delay in sequencing caused by the lengthy procedures of synthesis and purification of the walking primer.

The present invention addresses the following quantitative discrepancy in the walking primer method. On the one hand, the molar amount of a primer required for a typical reaction of enzymatic DNA sequencing is on the order of a picomole. On the other hand, the oligonucleotide synthesizers make a typical amount of primer between 0.2 and 1.0 micromoles. That is five to six orders of magnitude more than is required. People have given thought to this consideration, and suggested to create a library of primers, containing a sufficient variety of sequences to cover the needs of the walking primer method (Studier, W. 1989 Proc. Natl. Acad. Sci. USA 86, pp. 6917–6921). An advantage of such a library is, that only a minuscule part of a primer sample, is used for each sequencing reaction. Each primer sample is used many times, dramatically reducing the normally high cost of walking primer per reaction. The sequencing is also speeded up by the use of ready made primers.

However, it turns out that creation of such a library would be an enormous enterprise at the present synthesis capabilities. Indeed, a primer from such a library can have a reasonably unique priming site in most templates, only if it contains at least 8 or 9 nucleotides. The number of all possible 8-mers is about 64,000. Even if only a third of them, about 21,000 different sequences, are needed for a representative library, the synthesis of such a large number of oligonucleotides would be very expensive and time consuming. On the user side, storage and utilization of such a huge library would also present serious problems.

To overcome the problem of the large size and, therefore, the high cost of such a library, it was suggested recently (Szybalski, W. 1990 Gene, 90, pp. 177–178) to make 12-mer primer by ligating two 6-mer oligonucleotides annealed to the template next to each other. The two 6-mers were expected to be selected from a library of possible 6-mers. So far, to the best of my knowledge, the experiments with this technique (unpublished) showed that the efficiency of ligation of the two 6-mers on the template depends on the position of the priming site within the template. Sometimes this efficiency is prohibitively low. A dramatic drop in the ligation efficiency occurs, as the length of the ligated oligonucleotides is changed from 6-mer to 5-mer. Ligation of two 5-mers on the template usually does not work even when ligation of two 6-mers does, presumably, because the combined length of two adjacent 5-mers (10 nucleotides) is not long enough substrate for the ligase to work efficiently. However, even if a ligation technique is found to work efficiently, it would introduce a very inconvenient step of additional enzymatic reaction (ligation) in the sequencing.

The present invention obviates the need for such an additional enzymatic reaction (ligation) in the sequencing protocol. Moreover, the present invention allows oligonucleotides shorter than 6-mers to form a composite primer.

SUMMARY OF THE INVENTION

The present invention offers to overcome the foregoing problems by using a composite nucleic acid primer for priming a reaction of extension of the composite primer on a template strand of a nucleic acid with a nucleic acid polymerase enzyme. The composite primer comprises two or more covalently unconnected composing oligonucleotides, termed first oligonucleotide and second oligonucleotide, also termed auxiliary and priming oligonucleotides. They are also termed composing oligonucleotides. Each composing oligonucleotide comprises a binding segment of a base sequence complementary to a binding site in the template strand. The binding segment and the binding site are selected for binding of this composing oligonucleotide to the template strand by means of annealing between the binding segment and the binding site. The binding sites for different composing oligonucleotides are sufficiently proximal to each other in the template strand to enhance the sequence specificity of priming by the composite primer, as compared to the sequence specificity of priming by one of the composing oligonucleotides alone. The closeness is measured in terms of distance along the template strand.

In the preferred embodiment the composing oligonucleotides annealed to the template strand are base-stacked to each other. In another embodiment the composing oligonucleotides comprise mutually complementary segments. These complementary segments connect the composing oligonucleotides non-covalently, when the complementary segments are annealed to each other.

The composing oligonucleotides may comprise a modification of a natural chemical conformation of the nucleic acid. One possible modification may be needed to inhibit an enzymatic extension of the 3'-end of modified oligonucleotide. Another possible modification carries a fluorescent dye attached to the modified oligonucleotide. Still another modification carries a tag and a binding means, like biotin, attached to the tag, which means is able to bind another molecule to the tag.

Apart from the first and the second oligonucleotides, the composite primer can further comprise a third oligonucleotide, which possesses a binding site on the template sufficiently close to the binding site of one of the other two composing oligonucleotides for this third oligonucleotide to enhance the sequence specificity of priming by the composite primer as compared to a composite primer consisting of one of the composing oligonucleotide alone.

The binding sites for different composing oligonucleotides can be sufficiently close to each other in the template strand to enable the oligonucleotides to be in contact with one another while annealed to these binding sites. This contact should not be achieved by too bulky means like avidin and biotin, restrictive towards the functioning of the polymerase enzyme. In other words it should not present a physical obstacle for the polymerase function, but rather permit the polymerase to perform the primer extension reaction. This contact essentially serves as a link between the composing oligonucleotides for enhancing the sequence specificity of priming by the composite primer, as compared to the sequence specificity of priming by one of the oligonucleotides alone.

The composing oligonucleotides can be capable of base-stacking interaction with each other, when annealed to the template strand. Alternatively, two of the composing oligonucleotides can comprise mutually complementary segments, which connect non-covalently the two oligonucleotides, when the complementary segments are annealed to each other. Contacts by both base-stacking and annealing can exist between the same oligonucleotides.

In addition to the first and the second oligonucleotides, the composite primer can further comprise a third oligonucleotide, which possesses a binding site on the template sufficiently close to binding site of one of the other two oligonucleotides for the third oligonucleotide to be in contact with one of the other two oligonucleotides.

The present invention also includes a method of priming an extension reaction of a first strand of a nucleic acid by a nucleic acid polymerase enzyme on a template of a second strand of a nucleic acid. This method comprises:

a) Annealing the template strand to two or more covalently unconnected oligonucleotides, which are capable of forming a composite primer. Each composing oligonucleotide comprises a binding segment of a base sequence complementary to a binding site in the template strand. The binding segment and the binding site are selected for binding of this composing oligonucleotide to the template strand by means of annealing between the binding segment and the binding site. The binding sites for different composing oligonucleotides are sufficiently close to each other in the template strand to enhance the sequence specificity of priming by the composite primer, as compared to the sequence specificity of priming by one of the composing oligonucleotides alone. The closeness is measured in terms of bases along the template strand.

b) Extending the primer with the polymerase enzyme. The composing oligonucleotides in this invention remain covalently unconnected during the primer extension reaction, in contrast to the primer obtained by ligation of 6-mers in the Prior Art.

In this method the binding sites selected for the composing oligonucleotides are sufficiently close to each other in the template strand to enable the composing oligonucleotides to be in contact with one another while annealed to the selected binding sites. Yet this contact does not hinder the polymerase activity (as could happen, if the contact is achieved by streptavidin-biotin link, which introduces a bulky steric obstacle to the polymerase), but rather permits the nucleic acid polymerase to perform the primer extension reaction. This contact links the oligonucleotides for increasing the sequence specificity of priming by the composite primer, as compared to the sequence specificity of priming by one of the composing oligonucleotides alone.

In this method the composing oligonucleotides annealed to the template strand can be in contact by base-stacking interaction. Two of the composing oligonucleotides can comprise mutually complementary segments forming a link by annealing between the two oligonucleotides, when the complementary segments are annealed to each other. This link stabilizes the binding of the linked oligonucleotides to the template strand.

In this method at least one of the composing oligonucleotides can be modified, in such a way that the modification prevents an enzymatic extension of the 3' end of the oligonucleotide. At least one of the composing oligonucleotides can carry a fluorescent dye attached to it. At least one of the oligonucleotides can carry a tag and a binding means, attached to the tag, so that the binding means are able to bind an additional molecule to the tag. The binding means can in particular be biotin attached to the oligonucleotide by a chain of atoms which chain represents a tag. Generally in this method, at least one of the composing oligonucleotides can contain a chemical modification of a natural DNA conformation.

In this method, the composite primer can comprise, apart from two composing oligonucleotides, at least one additional oligonucleotide. This additional oligonucleotide possesses a binding site in the template sufficiently close to the binding site of one of the two other oligonucleotides for the additional oligonucleotide to enhance the sequence specificity of priming by the composite primer in comparison with priming without by one of the composing oligonucleotides alone.

The present invention also includes a composite nucleic acid probe for hybridization to a target nucleic acid strand. The composite probe comprises two or more covalently unconnected nucleic acid oligonucleotides, termed the first and the second oligonucleotides. The oligonucleotides forming the composite probe are also termed composing oligonucleotides. Each of the composing oligonucleotides comprises a binding segment complementary to a binding site in the target strand. The binding segment and the binding site are selected to bind the corresponding composing oligonucleotide to the target strand by means of annealing between the binding segment and the binding site. The binding sites for different composing oligonucleotides are close enough to each other in the target strand for the composing oligonucleotides to be in contact with one another, while annealed to these binding sites. This contact enhances the sequence specificity of binding by the composite probe to the target strand as compared to binding by one of the composite oligonucleotides alone.

In particular, two of the composing oligonucleotides can comprise mutually complementary segments. The complementarily enables the mutually complementary segments to anneal to each other, thereby noncovalently connecting the two composing oligonucleotides.

The composite probe can comprise, apart from the first and the second composing oligonucleotides, at least one additional composing oligonucleotide, also termed the third oligonucleotide. The additional composing oligonucleotide possesses a binding site on the template strand close enough to one of the binding sites of one of the other two composing oligonucleotides, for the additional oligonucleotide to be in contact with this other oligonucleotide and simultaneously to be annealed to its binding site.

The present invention also includes a collection of nucleic acid oligonucleotides, each oligonucleotide being shorter than six nucleotides in length, in which collection the base sequence of the oligonucleotides comprises a variable segment. The base sequence of the variable segment varies from one oligonucleotide to another within the collection. The collection contains at least two percent of all possible sequences of the variable segment and at least five different sequences.

This collection of oligonucleotides can be used for non-covalently forming a composite primer described in this invention, rather than for ligating the oligonucleotides into a covalently linked primer, which ligation usually requires the oligonucleotides to be at least six bases long. A collection containing less than two percent of all possible sequences of the variable segment is not useful. Nor is a collection containing less than five different sequences.

The present invention also includes a collection of nucleic acid oligonucleotides possessing a modification of a natural DNA conformation, which modification inhibits enzymatic primer extension of the 3'-end of the oligonucleotides. In this collection the base sequence of the oligonucleotides comprises a variable segment, base sequence of the variable segment varying from one oligonucleotide to another within the collection, the collection containing at least two percent of all possible sequences of the variable segment and at least five different sequences. This collection can be used for making the composite primer described in this invention and for priming a strand extension reaction by this composite primer.

The present invention also includes a set (combination) of a first and a second collections of nucleic acid oligonucleotides, all base sequences of oligonucleotides in the first collection comprising a variable segment and a first common segment, all base sequences of oligonucleotides in the second collection comprising a variable segment and a second common segment, the first and second variable segments' sequences varying from one oligonucleotide to another within each of the two collections;

the first common segment of the first collection being complementary to the second common segment of the second collection for connecting non-covalently an oligonucleotide from the first collection to an oligonucleotide from the second collection, when the complementary segments are annealed to each other.

The present invention also includes an apparatus for automatic sequencing of nucleic acids, comprising:

a) a first automated machine performing enzymatic reaction for nucleic acid sequencing by 3'-end extension of a primer annealed to a template strand of nucleic acid, chain terminating nucleotides being incorporated into the extended strand;

b) a second automated machine determining the base sequence of the template by comparing the lengths of the terminated fragments of the extended primer;

c) a first software means for selecting a sequence of a primer annealing site for composite primer within a known sequence of the extended strand, the primer annealing site being designated to anneal a primer for a reaction of the enzymatic extension further in 5' to 3' direction of the extended strand;

d) a second software means designing the composite primer to consist of at least two oligonucleotides, the oligonucleotides being selected to possess a substantially higher sequence specificity of priming when used together than either of them used alone.

e) a hardware means for pooling together samples of the two oligonucleotides selected by the second software means for performing the enzymatic primer extension.

In this apparatus the first automated machine can comprise a pipetting robot, while the second automated machine can comprise an electrophoresis device, a detector of electrophoretic bands in the electrophoretic device, and a computer for determining the nucleotide sequence of a segment of the enzymatically extended strand from the pattern of bands detected by the detector.

This apparatus can be geared to automatically perform the sequencing in cycles, advancing along the template strand; the cycle comprising the following steps:

a) selecting an annealing site within a known region of the template sequence for annealing of a composite primer;

b) selecting two or more oligonucleotide sequences for forming the composite primer able to anneal to the selected annealing site;

c) pooling together sample of the selected oligonucleotides to form the composite primer, by annealing the selected oligonucleotides adjacently to each other to the annealing site in the template strand for enhancing the sequence specificity of priming by the composite primer, in comparison with the sequence specificity of priming by either of the selected oligonucleotides alone; and d) performing the chain terminating sequencing reaction by enzymatically extending the primer along the template; electrophoresing the products of the reaction; reading the sequence of the primer extension region from the electrophoretic band pattern of the reaction products.

The present invention also includes a method for automated sequencing of nucleic acids by means of advancing along a template strand of nucleic acid in a mode of recurrent cycles of the walking primer technique; in which method stored collections of oligonucleotides are used for forming a composite primer comprising at least two covalently unconnected the oligonucleotides, the cycle comprising the following automated steps:

a) selecting an annealing site within a known region of the template sequence;

b) selecting at least two oligonucleotide sequences from the collections for forming the composite primer able to anneal to the selected annealing site;

c) pooling together samples of the selected oligonucleotides to form the composite primer, in which the oligonucleotides are annealed to the template adjacently to each other for enhancing the sequence specificity of priming by the composite primer, as compared to the sequence specificity of priming by one of the oligonucleotides alone; and d) performing a chain terminating sequencing reaction by enzymatically extending the primer along the template; electrophoresing the products of the reaction; reading the sequence of the primer extension region from the electrophoretic band pattern of the reaction products.

The present invention also includes a method of automated reading of sequence of a nucleic acid strand from a pattern of electrophoretic bands of products of chain terminating sequencing reactions of enzymatic primer extension on the template of this nucleic acid strand, in which method the reading of the sequence is facilitated by loading the products of the sequencing reactions terminated with more than one type of terminators into individual channels of electrophoresis, so that different channels may comprise electrophoretic bands resulting from the same type of terminators, as well as bands resulting from different types of terminators; signals from the different channels being synchronized by a computer by means of aligning and matching the bands originating from the same type of terminator.

Several objects of the present invention are:

(a) to eliminate the step of primer synthesis in the walking primer method of DNA sequencing;

(b) to avoid the need for an excessively large library of oligonucleotides (e.g. 8-mers, see above) for that purpose;

(c) to avoid an additional enzymatic step in DNA sequencing, like ligating two 6-mers on the template to make a 12-mer primer.

It is a further object of the invention to automate the walking primer technique of DNA sequencing by using a composite primer constructed from oligonucleotides selected from oligonucleotide libraries. The use of the composite primer makes it possible to advance along the template in a sequential (walking) manner, while obviating the need for primer synthesis step, thus conveniently allowing automation of the walking cycle. The purpose is to advance along the template automatically in a chain of sequencing reactions, each followed by an electrophoretic run.

The present invention offers a solution to the problem of the high cost of synthesis of non-composite primer library, like that of possible 8-mers. In comparison to the 8-mer oligonucleotide libraries for non-composite primer, libraries for composite primer described in the present invention can have about 2 orders of magnitude fewer samples, thus amounting to a manageable task in terms of synthesis. The method described below, allows one to construct a composite primer, which is sufficiently unique in terms of its priming site occurrence, and has adequate priming efficiency as well as high sequence specificity of priming.

An advantage of the invention is that the composite primer libraries, would raise manyfold the efficiency of the walking primer method of DNA sequencing. The breakthrough in the efficiency would be in terms of both cost and time. The cost reduction would come from the fact that the molar amount of primer in each sample in the library would be only a minuscule fraction of the amount synthesized. In contrast to that, now the walking primer user pays for the full amount of the synthesized oligonucleotide (5 to 6 orders of magnitude more than the user needs). As to the time, the saving comes from the instant availability of the primer to the user possessing the library, whereas now most users have to wait days between ordering and receiving a custom made primer. What makes the composite primer libraries feasible, is that they are many-fold smaller than the (so far unsynthesized) non-composite primer libraries, like those of 8-mers discussed above.

Still further objects and advantages will become apparent from a consideration of the ensuing description and drawings.

Figure 1:
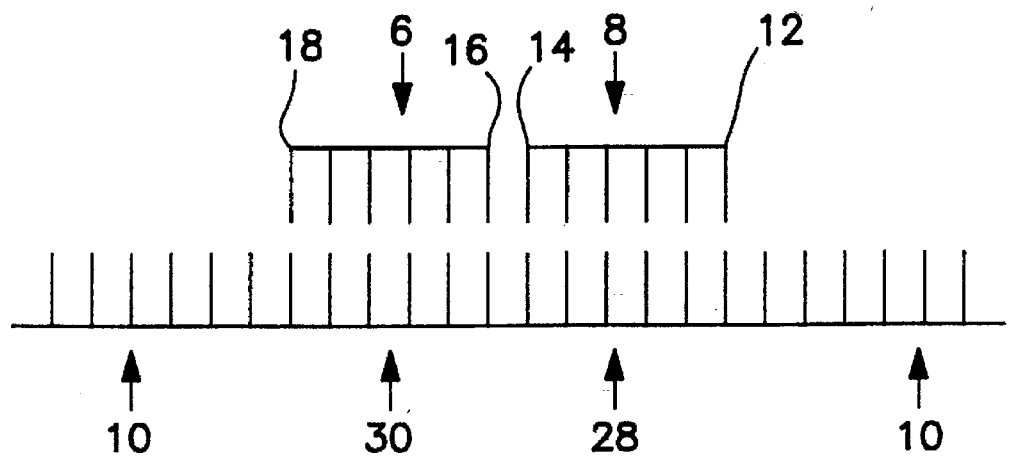
FIG. 1 shows schematically a composite primer consisting of two base-stacked oligonucleotides annealed to a template.

The following are reference numerals used in the drawings:

6 - auxiliary oligonucleotide
8 - priming oligonucleotide
10 - template strand of DNA
12 - 3'-end of priming oligonucleotide
14 - 5'-end of priming oligonucleotide
16 - 3'-end of auxiliary oligonucleotide
18 - 5'-end of auxiliary oligonucleotide
20 - holding segment
22 - supporting segment
24 - binding segment of priming oligonucleotide
26 - binding segment of auxiliary oligonucleotide
28 - binding site for priming oligonucleotide
30 - binding site for auxiliary oligonucleotide
32 - 3'-end of third oligonucleotide
34 - 5'-end of third oligonucleotide
36 - binding site for third oligonucleotide

DETAILED DESCRIPTION OF THE INVENTION

Method of priming of extension reaction by composite primer:

In this method the strand extension reaction is primed by a primer composed of two or more short composing oligonucleotides, selected from their corresponding libraries (banks of sequences). They are annealed to the template strand next to each other, while covalently unconnected. For this purpose, their sequences are chosen in such a way, that the composing oligonucleotides are complementary to adjacent binding sites in the template. Their proximity when annealed to these sites, makes the priming efficiency of the selected priming site superior to that of other binding sites of one or the other of these oligonucleotides randomly occurring elsewhere in the template. The superior efficiency results in priming, which occurs mostly at the annealing site selected for the composite primer, while priming elsewhere in the template, where the composing oligonucleotides could randomly anneal separately from each other, is weak if any. The occurrence of priming mainly at the selected annealing site results in an increased sequence specificity of priming achieved by the composite primer. Essentially, the utilization of closely annealed composing oligonucleotides (in the composite primer) increases the sequence specificity of priming as compared to the utilization of only one of these oligonucleotides.

An essential requirement in this method is that the selected site for annealing of the composite primer should be sufficiently unique in the template. That is, the occurrence within the same template of another site, similarly active in terms of priming with the same composite primer, should be rare. The uniqueness is mainly determined by a sufficient total length of annealing between the composite primer and the selected binding site in the template.

Preferred embodiment of composite primer:

FIG. 1 schematically shows a composite primer annealed to DNA template strand 10. The composite primer comprises two DNA oligonucleotides: priming oligonucleotide 8 with its 3'-end 12 and 5'-end 14, and auxiliary oligonucleotide 6 with its 3'-end 16 and 5'-end 18. Priming oligonucleotide 8 is complementary to priming binding site 28 in template strand 10. Auxiliary oligonucleotide 6 is complementary to auxiliary binding site 30 in template strand 10. Binding sites 28 and 30 form a continuous annealing site for the composite primer. In other words, priming binding site 28 is adjacent to auxiliary binding site 30, so that a non-covalent link (contact) by base-stacking interaction is established between priming oligonucleotide 8 and auxiliary oligonucleotide 6 upon their binding to sites 28 and 30 respectively. Priming and auxiliary oligonucleotides are also termed here and onwards the first and the second oligonucleotides. Both are also termed composing oligonucleotides. The number of composing oligonucleotides (oligonucleotides the composite primer composed of) does not have to be limited to two. For example, an additional 6-mer oligonucleotide, termed third oligonucleotide, can be fully annealed to template 10, while base-stacked to the 5'-end 18 of auxiliary oligonucleotide 6 shown in FIG. 1. In some embodiments the addition of the third oligonucleotide may be required to improve the performance of the composite primer.

EXAMPLE 1 OF PREFERRED EMBODIMENT

The following are examples of particular sequences of two base-stacked composing oligonucleotides annealed to the template as shown in FIG. 1. If the sequence of priming binding site 28 is, for example, 5'=A-C-A-C-G-T='3, then priming oligonucleotide 8 annealed to this site is of sequence 5'=A-C-G-T-G-T='3. If auxiliary binding site 30 has the sequence 5'=T-C-G-A-G-C='3, then auxiliary oligonucleotide 6 annealed to this site has the sequence 5'=G-C-T-C-G-A='3. Here and onwards the dash (–) denotes covalent link between two adjacent nucleotides of the same strand by sugar-phosphate backbone. 5'=denotes the 5'-end of an oligonucleotide. =3' denotes the 3'-end of an oligonucleotide. A, C, G and T denote adenine, cytosine, guanine and thymine. Priming and auxiliary binding sites 28 and 30 are adjacent to each other within DNA template strand 10. Together they form a continuous annealing site for the composite primer. Since these binding sites have no gaps between them, the composing oligonucleotides can base-stack to each other when annealed to these binding sites. The reference numerals refer to FIG. 1.

EXAMPLE 2 (ANOTHER EXAMPLE OF PREFERRED EMBODIMENT)

The following is another example of structure of composite primer:

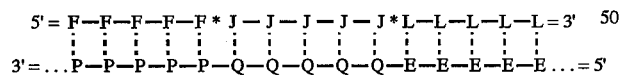

Here and onwards the asterisk (*) shows the base-stacking contact. The interrupted vertical bar character (¦) denotes Watson-Crick base-pairing between two nucleotides of opposite DNA strands in the DNA double helix. In this example the first (priming) oligonucleotide is shown as L-L-L-L-L. If its sequence is, for example, 5'=A-C-G-T-G= 3', then the complementary sequence of the first (priming) binding site, shown as E-E-E-E-E, is 5'=C-A-C-G-T=3'. If the second (auxiliary) oligonucleotide, shown above as J-J-J-J-J, has the base sequence 5'=A-G-C-G-A=3', then the second (auxiliary) binding site, shown as Q-Q-Q-Q-Q, has the sequence 5'=T-C-G-C-T=3'. If the third oligonucleotide, shown as F-F-F-F-F, is of the sequence 5'=C-G-G-T-A=3', then the third binding site, shown as P-P-P-P-P, to which the oligonucleotide is annealed, is of the sequence 5'=T-A-C-C-G=3'. Each of the composing oligonucleotides can be annealed to the corresponding binding site in the template.

These three binding sites are adjacent to each other in the template. They form a continuous annealing site for the composite primer. Since these binding sites have no gaps between them, the composing oligonucleotides are capable of base-stacking interaction with each other, when annealed to these binding sites on the template.

Oligonucleotide libraries:

An oligonucleotide library is a collection of samples, each sample containing oligonucleotides of a specific sequence. Priming oligonucleotide 4 and auxiliary oligonucleotide 6 are chosen from their respective libraries: the priming library and the auxiliary library. First, an annealing site, consisting of priming binding site 28 and auxiliary binding site 30 as shown in FIG. 1, is selected within a known region of template strand 10. The priming binding site within the selected annealing site for composite priming is also termed "selected priming site". Then, the sequences of priming oligonucleotide 4 and auxiliary oligonucleotide 6 are selected to be complementary to the sequences of sites 28 and 30 respectively. Within each library, the sequences of the oligonucleotides change from sample to sample, giving a choice of a large variety of sequences. In some cases, one library can serve as both priming and auxiliary libraries, if the length, structure and chemical requirements are similar for both priming oligonucleotide 4 and auxiliary oligonucleotide 6. The two binding sites 28 and 30 together, should be long enough to make the selected annealing site sufficiently unique within the entire template strand 10.

Priming efficiency:

While not wishing to be bound by theory, following are two of possible reasons why the priming efficiency of the composite primer at the selected annealing site is superior to the efficiency of either of its components annealed alone. Either of the two reasons can work separately, or both of them can work together:

Reason 1. The priming efficiency of an annealing site in the template depends, among other things, on the affinity of the primer to this site. Due to the link between the two composing oligonucleotides, shown in Example 1 (base-stacking), the priming oligonucleotide possesses a higher energy of binding to the template, if it is base-stacked to the auxiliary oligonucleotide, than if it is not. As a result, in presence of the auxiliary oligonucleotide, the occupancy of the selected priming site by the annealed priming oligonucleotide is much fuller than that of another priming binding site not adjacent to an auxiliary binding site. Thus, the priming efficiency of the annealing site selected for the composite primer dominates over randomly occuring unconnected binding sites for priming and auxiliary oligonucleotides, since these oligonucleotides have a higher affinity to the template when connected than when unconnected to each other. It also dominates over the sites of partial binding (with mismatches) of the composite primer as a whole (two linked composing oligonucleotides) or the priming oligonucleotide alone. Here and below we assume for simplicity that the template is single-stranded, although composite primers can work in double-stranded DNA sequencing too.

The primer-to-template annealing reaction is often carried out by gradually decreasing the temperature prior to the primer extension reaction. The priming and auxiliary oligonucleotides annealed to the template, have a higher melting temperature when connected than when unconnected to each other. When the temperature is gradually lowered in the annelaing reaction, the annealing of the priming and auxiliary oligonucleotides to the template occurs earlier at the adjacent binding sites than at separated sites. This difference in the annealing temperature can shift the preference in the site of primer annealing towards the site selected for the composite primer, as compared with randomly occurring sites complementary to the priming oligonucleotide.

Reason 2. The priming efficiency of a base-stacked composite primer has another reason for being superior to that of its unconnected parts annealed separately. DNA and RNA polymerases generally prefer longer primers to short ones as substrates for a primer extension reaction. For example, a 12-mer composite primer consisting of two base-stacked 6-mers is preferred by Sequenase to a separately annealed, 6-mer, unconnected to other oligonucleotides. That reason makes the priming efficiency of adjacently annealed composing oligonucleotides superior to priming efficiency of the priming oligonucleotide annealed alone, whether at the selected priming site or elsewhere. In this respect, what makes the selected annealing site special is the possible presence of an auxiliary oligonucleotide annealed just next to the priming oligonucleotide. The polymerase preference for longer primers favors composite primer designs involving three or more composing oligonucleotides. For example, a composite primer consisting of three base-stacked pentamers may have a crucial advantage in terms of priming efficiency over two base-stacked pentamers, with some DNA polymerases, like Sequenase.

This second reason, the DNA polymerase preference for longer primers, is qualitatively different from the first reason, the enhancement of annealing of composing oligonucleotides by their base-stacking. The second reason does not require the annealed composing oligonucleotides being physically linked with each other, but rather being close enough.

Whichever of the two reasons dominates under a particular set of conditions, the superior priming efficiency of the composite primer, as compared to either of the composing oligonucleotide alone, changes their uniqueness as primers. It makes the composing oligonucleotides work, when added together into a primer-extension reaction, more like one long primer uniquely annealed at the selected site. Although each of the composing oligonucleotides is short and technically able to anneal randomly in the template, when taken together they can work as a unique long primer due to the presence of the selected annealing site which brings them together.

Sequence specificity of priming:

The priming oligonucleotide used alone, may possess more than one priming site (complementary to this oligonucleotide) in the template, where it can anneal and serve as a primer. These priming sites are generally given equal opportunities to attract the priming oligonucleotide, although the priming occurs in some of them somewhat better than in others for such reasons as the template secondary structure, the sequence environment and other factors. When several such priming site are present in the template, more than one of them usually have comparable priming efficiency. Similarly, the auxiliary oligonucleotide, like the one shown in FIG. 1, can display more than one site of priming, when used alone, if it can be enzymatically extended as a primer.

Much more sequence specific priming occurs, when the priming oligonucleotide is used together with the auxiliary oligonucleotide, than when one of the two oligonucleotides is used alone. The increased sequence specificity means that a relatively much stronger priming occurs at the selected priming binding site, where the two composing oligonucleotides are annealed to the template close to each other, as compared to other possible priming sites in the template, where the priming oligonucleotide anneals with no auxiliary oligonucleotide next to it. The increase in the sequence specificity of priming by the composite primer at the selected annealing site, is a result of the proximity to each other of the composing oligonucleotides annealed at this site.

The strength of priming is reflected in the relative intensity of different electrophoretic band patterns on a sequencing gel, corresponding to different priming sites. These different band patterns are superimposed on each other, and their relative intensity shows the priming efficiency of different priming sites. If the template sequence near the selected priming site is known, the distinct band pattern corresponding to this site can be compared in strength with band patterns of other priming sites, whether known or unknown. This comparison represents a measure of whether the composite primer works properly, that is sequence specifically, or not. In other words, this test checks whether the known band pattern of the selected priming site sufficiently dominates in strength over the band patterns of other possible priming sites. Reading the sequence primed at the selected priming site is made possible, when the domination is sufficient, that is, when the difference in strength between the bands arising from the selected priming site and other priming sites, if there are any, is large enough.

For a more general design of composite primer which may consist not of just two, but of, generally speaking, two or more composing oligonucleotides, the sequence specificity has a similar property. The priming oligonucleotide displays a higher sequence specificity of priming when used together with all the composing oligonucleotides constituting the composite primer, than used in the absence of one or more of the composing oligonucleotides. The binding sites for the composing oligonucleotides are selected close enough to each other in order to give the composite primer this increased sequence specificity.

For some template sequences, the priming oligonucleotide used alone results in weaker priming at the selected priming site than at some other sites where it anneals. But when it is used in combination with the auxiliary oligonucleotide, as a part of the two component composite primer, it gives a much stronger priming at the selected priming site than elsewhere.

In very rare cases, there may occur a priming site other than the selected one, where the composing oligonucleotides happen by chance to anneal as close to each other as in the selected annealing site. The occurrence of such a priming site would make this particular composite primer similarly sequence specific to that particular site as to the selected priming site. The probability of such occurrence in a random template sequence depends on the uniqueness of the composite primer, which is determined by the total annealing length of the composing oligonucleotides, excluding degenerate base positions. This probability is similar to the probability of a conventional primer of the same length to find a perfect annealing site other than the site designed for this conventional (non-composite) primer.

Sizes of libraries of composite primers:

For the composite primer consisting of two base-stacked 6-mers shown above, the two 6-mer oligonucleotide libraries can be, for example, of the following structure. The priming library of oligonucleotides has the structure 5'=A-N-N-N-N-N=3'. It means that, of the six nucleotides, one, sitting on the 5' end, is fixed. In this example it is adenine, shown as A. This 5'-terminal position has the same base in all the samples of the priming library. The other five positions form a variable segment, that is a segment in the composing oligonucleotide, whose base sequence varies from sample to sample. Each of these five positions, shown as N, is a variable position, which means that it's base may change from sample to sample within the library, being either A, C, G, or T, depending on the sample sequence. Different combinations of bases in the variable positions can form all possible sequences of the 5-mer N-N-N-N-N variable segment, $4^5$ possible combinations, within the 6-mer 5'=A-N-N-N-N-N=3'.

The absence of variability in the 5'-terminal position, which has A-base in all samples of this example, is introduced in order to reduce the number of samples in the library by a factor of 4. The reduction is from $4^6$ samples in a complete 6-mer library of the 5'=N-N-N-N-N-N=3' structure, down to $4^5$ samples in the reduced library of the 5'=A-N-N-N-N-N=3' structure adopted in this example. The price we pay for that reduction is the loss of about ¾ of all possible 6-mer binding sites in a random template sequence. After such 4-fold reduction we are still left with a whole quarter of all 6-mer binding sites in a random template. Thus, on the average, every forth base in a random sequence template is T and can be the 3'-end base of a 6-mer binding site for our priming library. This should be more than sufficient to select a single 6-mer priming binding site within a known sequence stretch, usually at least dozens bases long. It's preferable to avoid annealing sites involved in stable secondary structures of the template, like hairpins. Computer programs are available for estimating the secondary structure potential of a given sequence.

The following example of the auxiliary library demonstrates another possible way to reduce the size of oligonucleotide library. In this example, the auxiliary library has the oligonucleotide structure of 5'=X-N-N-N-N-N=3'. Here, X denotes a degenerate position at the 5'-terminus of the 6-mer long oligonucleotide. A degenerate position is a mixture of two or more of the four possible bases, A, C, G, and T. One way to make a degenerate position is to use a mixture of some or all of the four bases in the synthesis of this position in the oligonucleotide. Another way is to mix non-degenerate oligonucleotides differing in this base, after their synthesis. In this example, the 5' terminal nucleotide has all four possible bases mixed in equal proportions in each sample of the auxiliary library. The other five positions, shown as N-N-N-N-N, form a variable stretch within the auxiliary oligonucleotide. They can have either A, C, G, or T base, but not mixed in a single sample, in each of the five variable positions of the oligonucleotide 5'=X-N-N-N-N-N=3'.

Therefore, although both priming and auxiliary libraries consist of 6-mer oligonucleotides, only 5 out of the 6 positions are variable from sample to sample. All possible sequences of the five variable positions, N-N-N-N-N, can form $4^5$=1024 sequence samples in each of the two libraries. If either of the two libraries, priming or auxiliary, were complete, that is contained all possible sequences of the annealed length, six bases long, it would consist of (contain) $4^6$=4,096 sequence samples. In practice though, libraries do not have to be complete. Some of the sequences may or should be absent from the libraries. For example, a sequence containing a CGCG stretch may be chosen not to be represented in a library because of its rare occurrence in genomes. Or, a particular sequence may happen to have a lower efficiency than others as a component of the composite primer and be excluded from a library for that reason. Pyrimidines, for example, generally have lower base-stacking energy then purines, and may be excluded from the corresponding terminal positions in a particular library embodiment. Or, some sequences may inhibit a DNA polymerase activity as a result of sequence dependent curvature of the double-stranded DNA (L. Ulanovsky et al., 1986, Proc. Natl. Acad. Sci USA, Vol. 83, pp. 862–866, L. Ulanovsky and E. Trifonov, 1987, Nature, Vol 326, pp. 720–722). Or, some sequences may be excluded from a library just in order to reduce the size of the library. For example, the above structure 5'=A-N-N-N-N-N=3' of the priming oligonucleotide library can be viewed as exclusion of all 6-mer sequences starting from C, G or T base from a complete library of all possible 6-mers 5'=N-N-N-N-N-N=3'. The purpose of that particular exclusion is, as mentioned above, to reduce the library size to ¼ of the complete library size. The reduction of the library size can also be achieved by imposing a limit, either a minimum or a maximum, on the G+C content in the oligonucleotides, or by imposing another restriction or a combination of restrictions on the oligonucleotide sequences in the library.

Different schemes of reduction in library size can supplement each other. For example, the reduction by fixing the 5'-terminus position base, discussed above, can be followed by a further reduction in the library size by limiting the G+C content of the library sequences. However, reduction of a library to a too small size reduces the usefulness of the library for DNA sequencing purposes. Indeed, a library containing less than 2% of the all possible sequences of the variable segment can serve less than one in fifty possible binding sites for the particular composing oligonucleotide in a random sequence template. The portion of the sites the library can serve is even smaller, if the library structure contains a fixed base position, as in the priming library example above. Such a small size can make it difficult to select an annealing site for composite primer within a newly sequenced template stretch, which is often short. A library should also have a reasonable absolute size to be useful. It should contain at least five different sequence samples to be of practical use.

In example 1 above, the binding sites for both priming and auxiliary oligonucleotides are 6-mers (6 and 6 bases). In another embodiment, the corresponding lengths of the two binding sites can be 5 and 7 bases, such as 5'=A-N-N-N-N=3' in priming and 5'=X-X-X-N-N-N-N=3' in auxiliary libraries. In different embodiments, the lengths of the priming and auxiliary binding sites also can differ from the examples above, e.g. it can be 4 and 6; or 5 and 6; or 6 and 5 bases and other combinations. Generally, the sizes of the priming and auxiliary libraries may be the same as, or different from the examples above.

The number of composing oligonucleotides in the composite primer can be two, three or more. Their structures, and in particular lengths, can be different from each other. Therefore, sometimes, three or more oligonucleotide libraries can serve a single design for composite primer. For example, a three piece composite primer can be served by three libraries: a priming library of 5-mers, a first auxiliary library of 6-mers with one degenerate position, and a second auxiliary library of 7-mers with two degenerate positions.

Figure 2:
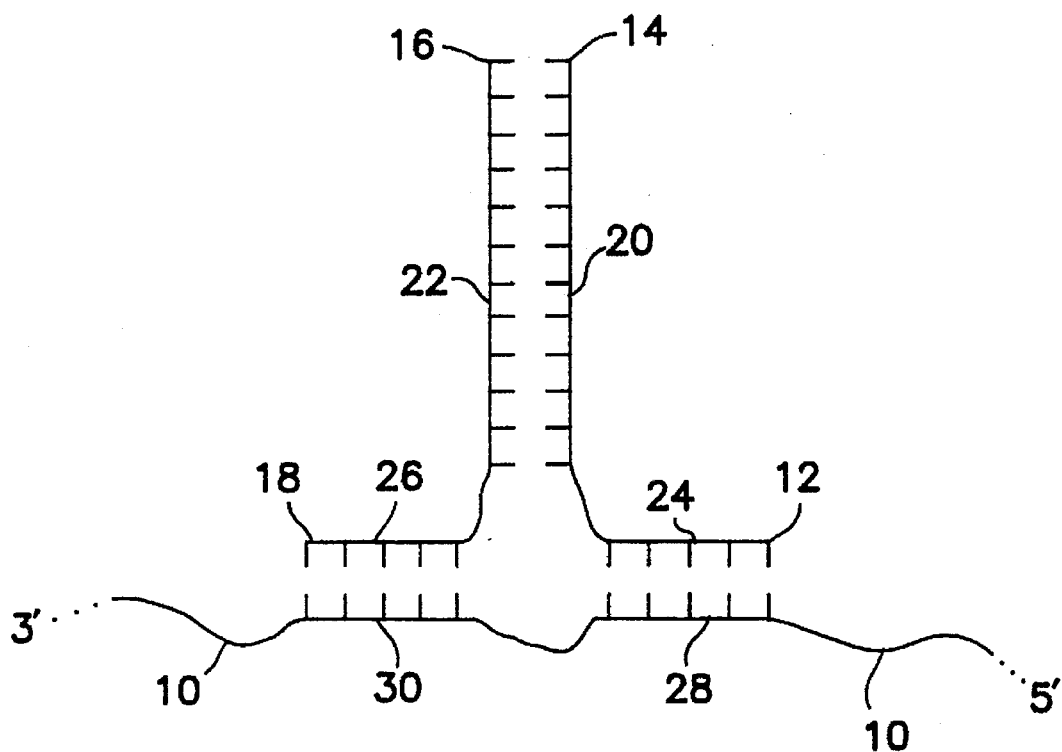
FIG. 2 shows schematically a composite primer consisting of two oligonucleotides annealed to each other and to a template.

Another embodiment: (composite primer formed by annealing between composing oligonucleotides):

FIG. 2 schematically shows another embodiment of a composite primer annealed to template strand 10. In contrast to the preferred embodiment shown above, this composite primer is kept together by annealing between its composing oligonucleotides, rather than by base-stacking interaction. This composite primer comprises two oligonucleotides: the priming oligonucleotide with its 3'-end 12 and 5'-end 14, and the auxiliary oligonucleotide with its 3'-end 16 and 5'-end 18. The priming oligonucleotide comprises holding segment 20 complementary to supporting segment 22 in the auxiliary oligonucleotide. FIG. 2 shows holding segment 20 annealed to supporting segment 22. The priming oligonucleotide further comprises binding segment 24 complementary to its binding site 28 in template strand 10. The auxiliary oligonucleotide comprises binding segment 26 complementary to its binding site 30 in template strand 10. In this embodiment the binding segment is a part of the composing oligonucleotide, whereas in the preferred embodiment of base-stacked oligonucleotides above, the entire composing oligonucleotide is a binding segment. Notation Z will be used below to denote a nucleotide (if there is any) connecting the binding segment with the rest of the oligonucleotide.

The supporting and the holding segments can also have different sequences and lengths from this example. It is desirable to design these sequences so that the two segments would not fold into stable secondary structures. It is also desirable to avoid slippages (shifts) in the annealing of the two segments to each other. For example, if the holding segment consists of all A's, while the supporting segment consists of all T's, their annealing to each other can easily shift by one or two bases. Oligonucleotides can be synthesized by methods well known to those skilled in the art and can be custom ordered from numerous companies (e.g. Clontech, Calif., USA).

Oligonucleotide libraries for composite primers formed by annealing:

In order to bind to the selected priming site, composed of segments 28 and 30 in FIG. 2, both the priming oligonucleotide and the auxiliary oligonucleotide are chosen from their respective libraries: the priming library and the auxiliary library. All the sequences in the priming library contain the same sequence of holding segment 20. All the sequences in the auxiliary library contain the sequence of supporting segment 22 complementary to holding segment 20. Therefore, regardless of a particular choice of the two samples from the two libraries, holding segment 20 anneals to supporting segment 22.

In contrast to segments 20 and 22, binding segments 24 and 26 vary within each library, their sequences changing from sample to sample. When a particular composite primer is being selected from the two libraries, binding segments 24 and 26 are chosen to be complementary to binding sites 28 and 30 in a known region of template strand 10. The two segments annealed to binding sites 28 and 30 should be long enough to make the selected annealing site sufficiently unique within the entire template strand 10.

Uniqueness of the annealing site:

In the example above, the selection of a annealing site involves choosing two close 5-mer binding sites in the template: for a priming and an auxiliary olitonucleotides. These oligonucleotides are then selected from their libraries to have their binding segment sequences complementary to their binding sites in the template. Such an annealing site is sufficiently unique for a plasmid clone, in the sense that the occurrence of an undesirable second annealing site for a selected composite primer is rare enough for sequencing purposes. However, this kind of annealing site is not unique enough for a YAC (Yeast Artificial Chromosome) clone, because YAC may be up to two orders of magnitude larger than a typical plasmid. For a cosmid clone, it may or may not be unique enough, depending on the size of the insert and on the allowed average occurrence of a second annealing site.

For a composite primer to have a sufficiently unique annealing site within a YAC clone, the total primer-to-template annealing length excluding degenerate positions should be several bases greater than 10. That requires much larger libraries, both priming and auxiliary, which may be justified for large scale sequencing projects.

Figure 3:
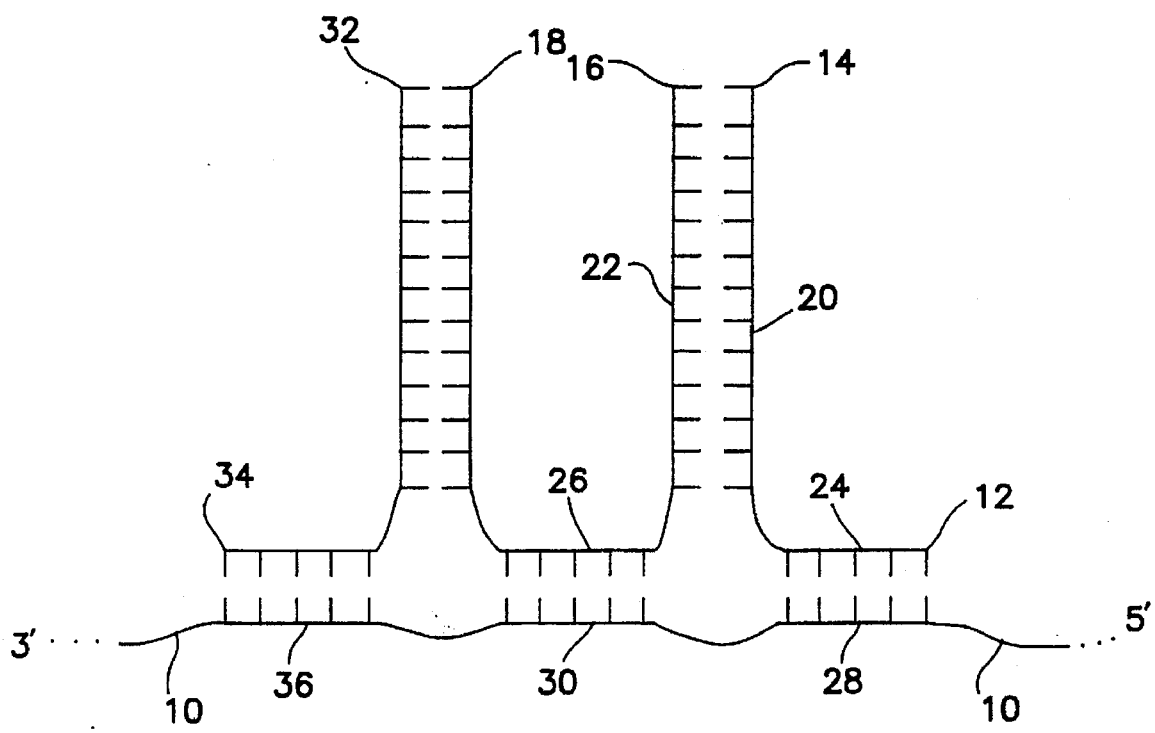
FIG. 3 shows schematically a composite primer consisting of three oligonucleotides annealed to each other and to a template.

Another possible solution for YAC's is to construct a composite primer of more than two oligonucleotides, for example three, as shown in FIG. 3. The third oligonucleotide can be seen in FIG. 3 with its 3'-end 32 and its 5'-end 34. It has a binding site 36 in the template, close enough to the binding site of the auxiliary oligonucleotide, for the third and the auxiliary oligonucleotides to be in contact with each other while annealed to the template. This contact is maintained by annealing a part of the third oligonucleotide to an additional segment of the auxiliary oligonucleotide specially added to its 5'-end in the scheme of three oligonucleotide composite primer, as shown in FIG. 3. This additional segment of the auxiliary oligonucleotide has the same sequence in all samples of the auxiliary library, this sequence being complementary to a segment in all samples of the third oligonucleotide library.

If each of the three oligonucleotides has a pentamer binding site with no degenerate positions, the total unique primer-to-template annealing length is 15 bases. This greater annealing length enhances the priming efficiency by strengthening the binding of the composite primer to the template. It also makes the composite primer sufficiently unique for YAC's. The uniqueness is sufficient even if there are two variable short gaps between the binding pentamer sites lowering the uniqueness.

In the same manner, a composite primer structure can contain four or more oligonucleotides. Each additional oligonucleotide is connected with the preceding one by annealing of their complementary segments. The binding site for the additional oligonucleotide is selected in the template sufficiently close to that of the preceding oligonucleotide to maintain contact between the two oligonucleotides, while maintaining their annealing to the template.

A composite primer of that kind, consisting of 3 or 4 oligonucleotides may be useful for plasmid size templates as well. For short templates, like plasmids, each of these oligonucleotides can have as short as 4-base binding site, with N-N-N-A type variable segment. A library of all possible combinations of the 3-mer N-N-N has only $4^3=64$ samples, which makes it more affordable to users, than the larger libraries of the 4-mer N-N-N-N.

Connecting nucleotides in composite primer formed by annealing between oligonucleotides:

In the example above, the nucleotide Z connecting the variable segment with the rest of the oligonucleotide can have any base, but preferably such modification, as Inosine or Deoxynebularin (both available from Glen Research Corp., Va., USA), which have weak base-pairing with the 4 normal bases. Z can also be a branched chain amino linker with no base at all, like "AminoModifier II", available for DNA synthesis from Clontech, Calif., USA. The purpose of the weak base-pairing of Z is to make the annealing site more unique. Otherwise, that is if Z has one of the 4 normal bases without weakened base-pairing, it can generate undesirable extra binding sites together with nucleotides adjacent to it.

In the example above, the connection between the variable segment and the rest of the oligonucleotide consists of one nucleotide Z. However, in other schemes it may consist of more than one, or no nucleotide at all. For example, for reasons of the polymerase activity or/and stability of the primer-template complex, tight base-stacking may be desirable between stems 20-22 and 24-28 in FIG. 2. This would require the absence of the Z nucleotide in the priming oligonucleotide. On the other hand, the steric interaction of a particular polymerase with the double helix may require more than one Z nucleotide in the auxiliary oligonucleotide to keep its second stem, 26-30, further away.

Contact by both annealing and base-stacking interactions:

The contact between priming and auxiliary oligonucleotides within a composite primer can be maintained in more than one way. Apart from annealing some parts of the two oligonucleotides together, the contact can be by base-stacking interaction between segments annealed adjacently to the template. If the binding segments 28 and 30 in FIG. 2 have a zero gap between them, the base-stacking of segments 24 and 26 may contribute to the stability of the primer-template interaction. If the stacking bases are purines, as in the example above, the energy contribution of their stacking into the primer-to-template binding is significant. The energy contribution of the base-stacking effectively minimizes the relative priming activity of undesirable secondary annealing sites, unless, by chance, these sites also have a zero gap between the binding segments 28 and 30. This improves by about an order of magnitude the uniqueness of the selected annealing site, where such gap is zero. Three oligonucleotide composite primer with one of the contacts by base-stacking only:

Another embodiment of the invention is a composite primer consisting of three oligonucleotides, two of which would look like in FIG. 2. The contact between them is by annealing their complementary segments. The third (priming) oligonucleotide would be a 6-mer. Its 5'-end base would have a base-stacking contact with the 3'-end of segment 24 of FIG. 2, when both of these oligonucleotides are annealed to their selected binding sites in the template. The 3'-end of segment 24 should preferably be modified to inhibit enzymatic extension of its 3'-end. This three oligonucleotide scheme has a more annealing site and a higher priming activity than the two oligonucleotide base-stacking scheme.

Apart from base-stacking and annealing, other types of link between oligonucleotides are possible. For example, antiparallel G-quadruple-strand link is possible between the holding and the supporting segments. Of the four strands, two antiparallel strands can come from the holding segment folded on itself while the other two come from similarly folded supporting segment.

Labels, tags and chemical midifications:

The composite primers can be used with many labels and tags used with conventional primers. The priming oligonucleotide can be made radioactived prior to the sequencing reaction, for example by phosphorylation with readioactive phosphate $^{32}P$, as described above. In other embodiments different isotypes, like $^{35}S$ can be used. For some automated sequencing machines the priming oligonucleotide in the composite primer can carry a fluorescent label near its 5'-end. For chemiluminescent detection the priming oligonucleotide in the composite primer can carry a tag (a chain of atoms) with a binding group, like biotin, sitting on it. Alternatively, the binding group can be a chemical functional group, like amino group, or carboxyl group, which can covalently bind various molecules. Biotin binding group can later bind a chemiluminescent molecule in a standard procedure of chemiluminescent detection. The biotin attached to the priming oligonucleotide can also be used to bind streptavidin for DNA trapping electrophoresis (Ulanovsky, L. et al. 1990 Nature 343, pp. 190–192). In some embodiments, like the base-stacked composite primers described above, the combination of a short priming oligonucleotide with a bulky label or tag linked to this oligonucleotide, may create a hindrance for some DNA polymerases, which polymerases would otherwise (without this bulky label) work well. In such a case, it may be preferable to put the label or the tag on the chain terminator (e.g. dideoxy dNTP).

A modified base, possessing enhanced base-stacking can be used in order to strengthen the base-stacking link between the composing oligonucleotides. For this purpose, a modified base, like 5-fluorodeoxyuridine, may be incorporated during the synthesis in the corresponding 5' or 3' terminal positions of the oligonucleotides. Such a base may have different (e.g. partially degenerate) base-pairing properties, which should be taken into account.

In some embodiments of the base-stacked composite primer, auxiliary oligonucleotide can have a chemical modification inhibiting enzymatic extension of its 3'-end. Such a modification may be needed to suppress the priming activity of the auxiliary oligonucleotide, when its 3'-end is not stacked to the priming oligonucleotide. The inhibiting modification can be useful, for example, for having a many-fold excess of the auxiliary oligonucleotide over the priming one, while the DNA label is incorporated by the DNA polymerase into the growing DNA strand. With such an excess, without the inhibition of the auxiliary oligonucleotide extension, undesirable priming at extra annealing sites can arise. The inhibiting modification can be, for example, the "3'-Amine-ON" AminoModifier, commerically supplied for oligonucleotide synthesis by Clontech, Calif. Another way to make an inhibiting modification is to incorporate a dideoxy nucleotide at the 3'-terminal position of the auxiliary oligonucleotide by terminal transferase, whereas the rest of the oligonucleotide has been chemically synthesized in a conventional manner. The modification which inhibits the 3'-end extension of an auxiliary oligonucleotide, should not prevent or too much inhibit polymerase enzyme from extending a short priming oligonucleotide base-stacked to the modified 3'-end of the auxiliary oligonucleotide.

An oligonucleotide library, as well as a single oligonucleotide can comprise one or more of these labels, tags an modifications. The labeled or modified oligonucleotide libraries can be built in more than one way. The modification, the tag or the label can be:

1. incorporated into the oligonucleotide during the synthesis of the oligonucleotide (e.g. biotin, aminomodifier II);
2. chemically linked to the oligonucleotide after the synthesis (biotinylation of primary amino group incorporated during the synthesis);
3. enzymatically incorporated into the oligonucleotide after the synthesis of the oligonucleotide (e.g. terminal transferase mediated incorporation of dideoxy nucleotide triphosphate or of biotinylated dNTP).

Example of procedure of DNA sequencing using composite DNA primers consisting of two base-stacked oligonucleotides:

Following is a technique for performing primers annealing reaction, and primer extension/termination reaction as two different reactions separated in time.

First, a region of template 10, where the base sequence is known, is scanned in order to select an appropriate annealing site for composite primer. The selected annealing site consists of two stretches: priming binding site 28 and auxiliary binding site 30 as shown in FIG. 1. These binding sites are selected to the adjacent to each other. Suppose, their sequences are selected to be as shown in Example 1. Priming oligonucleotide 4 and auxiliary oligonucleotide 6 are then selected as shown in Example 1 too and synthesized by a standard oligonucleotide synthesis technique, or aliquoted from their stocks, or from oligonucleotide libraries. Their sequences are complementary to the sequences of priming binding site 28 and auxiliary binding site 30 respectively. These two DNA oligonucleotides are then used together as a composite primer for single-stranded DNA sequencing. Radioactive labeling is done by transferring $^{32}$P from Gamma-$^{32}$P-ATP to the 5' terminus of the priming oligonucleotide by a standard reaction with T4 polynucleotide kinase. The kination should be as complete as possible, preferably with a chase reaction in excess of cold ATP.

The primer-to-template annealing reaction is then performed by cooling from 95° C. down to 10° C. within 10 to 30 minutes. The cooled samples are spinned down and kept on ice while ice cooled sequencing reaction components are added. The sequencing reaction is performed by a conventional single-step protocol, widely used with a variety of DNA polymerases. "Single-step protocol" means that primer extension chain termination are performed in a single reaction. The single step protocol is chosen in this case, since the radioactive labeling has already been done. For this reaction, all four nucleotide-triphosphates, namely dATP, dCTP, dGTP and dTTP, are taken non-radioactive, in preferably high concentrations. Analogues of natural dNTP, like deoxy inosine triphosphate or deaza-7'-dGTP can also be used. In each of the four termination samples, the ration of the concentrations of the dideoxy nucleotide-triphosphate (ddNTP) and the corresponding deoxy nucleotide-triphosphate (known as ddNTP-to-dNTP ratio) is as required by the polymerase protocol. Preferably, the DNA polymerase known as Sequenase (a modified T7 DNA polymerase) can be used in the single-step reaction. Other DNA polymerases with their single step sequencing protocols can be used as well, like the large fragment of *E coli* DNA polymerase I (Klenow), Reverse Transcriptase, BST polymerase, bacteriophage T7 DNA polymerase and others. During the sequencing reaction, the temperature of the samples, initially kept on ice, is gradually increased to 35°–65° C. depending on the polymerase optimal temperature. The termperatured increase takes from 10 minutes for highly processive polymerases, like Sequenase, to an hour for slow polymerases, like Klenow.

Alternatively, instead of the 5'-end labeling by kinase, alpha-$^{32}$P-dATP can be used to incorporate the radioactivity into the newly polymerized strand during the primer extension reaction. That can be done either in two step or preferably in one step reaction protocol. Another isotope, like $^{35}$S, can alternatively be used instead of $^{32}$P.

The lengths of the terminated products of the primer extension reaction are then analyzed by regular sequencing gel electrophoresis. After an X-Ray film is exposed to the gel, the film is developed and the template sequence is read from the band pattern of the four termination lanes. Each band corresponds to the fragment length from the 5'-end of the priming oligonucleotide to the termination point.

Following are some procedural details for sequencing with a composite primer consisting of two base-stacked oligonucleotides.

Details of the annealing reaction for single-stranded DNA template:

1. Two oligonucleotides are used here for a composite primer: the priming oligonucleotide and the auxiliary oligonucleotide, as described above, instead of one oligonucleotide, which is used as a primer in standard protocols, 2. The auxiliary oligonucleotide is taken in a ten fold excess over the template, which is in molar parity with or in a slight excess over the priming oligonucleotide as in protocols for regular primers. The components of the annealing reaction and then the sequencing reaction are taken in regular molar concentrations as in standard single-step protocols, well known for individual DNA polymerases.

3. A 1000 ml beaker is filled with 50–300 ml of water. The amount of water in the beaker determines how quickly the beaker will be cooled by the ambient air. A thin sheet of styrofoam able to float in the beaker is prepared. Holes are made in the styrofoam sheet to keep microtubes floating vertically half submerged in the water. The beaker is heated to 95° C. The microtubes with the prepared annealling mixture are inserted into the holes of the styrofoam sheet and put floating vertically on the surface of the 95° C. water.

4. The upper half of each microtube should be surrounded by the air, whereas the lower half is submerged under water. The beaker is not covered but rather is left open for the duration of annealing. The reason is that condensation of evaporated liquid on the inner surface of the top of the microtube, increases the concentration of the annealing mixture at the bottom. The increase in the concentration in the annealing mixture increases the sequence specificity of the annealing of the composite primer to the selected annealing site. Smaller starting volume of the annealing reaction, preferably at 5 ul, facilitates the increase in the concentration by evaporation. Preferably the starting volume of the annealing reaction is kept at 5 ul. That can be done either by scaling down the annealing and sequencing reactions, if required, which usually still gives a sufficient amount of product, or by splitting the standard reaction volume into 5 ul aliquots for annealing and then merging them together for primer extension reaction.

5. The beaker is cooled slowly by the ambient room temperature air, while being constantly stirred. The temperature of the water in the beaker is monitored. After the temperature slowly decreases to 35° C., which should take 10 to 30 minutes, the beaker is put into a large bowl of ice water, while still being stirred. The temperature in the beaker starts to fall and after it reaches 10° C., the microtubes are quickly put on ice, spinned down in a cold room and put back on ice.

Details of the extension-termination reaction:

Ice cooled components of standard single-step sequencing reaction are then added to the annealing mixture kept on ice. Although component concentrations used in regular protocols can be used, it is preferable to use lower NaCl concentrations to minimize secondary priming by individually annealed composing oligonucleotides. After the last component, usually the polymerase enzyme, is added, the microtubes are put floating as before into a 1000 ml beaker filled with ice cold water (with no ice). The beaker is then placed into a thermostated water bath maintained at the temperature optimal for the DNA polymerase used in the sequencing reaction. The temperature in the beaker starts to rise to allow the primer extension reaction to take place. The volume of water in the 1000 ml beaker is chosen to result in the temperature rise time (required to reach the temperature plateau in the beaker) about as long as the reaction duration required by the DNA polymerase at its optimal temperature. After the beaker temperature becomes close to the optimal temperature plateau (the water bath temperature), the reaction is continued at this temperature for another period of time again approximately equal to the duration of the reaction required by the DNA polymerase. A regular stop solution is then added to stop the reaction.

Technique of gradual decrease of temperature in a combined reaction of primer annealing and extension:

Following is a procedure of performing annealing reaction and primer extension/termination reaction in one step. Selection of oligonucleotides and their kination is done as above.

It is not always easy to determine the optimal temperature of the composite extension reaction a priori. One practical way to perform the reaction is to decrease the temperature slowly (within a few minutes to a few tens of minutes) through the right range. The starting temperature should be above the dissociation point of the complex of either of the oligonucleotides with the template (above 37° C. is usually high enough). After the template DNA is boiled for two minutes, it is mixed with the primer extension reaction components, including the DNA polymerase, in an eppendorf tube immersed floating in 40° C. water in a 1000 ml beaker with a spinning magnetic stir-bar. After the polymerase enzyme is added (last), the 40° C. beaker is put into an ice bucket filled with ice. The beaker starts to cool slowly, while being stirred, till its temperature approaches 25° C., when a standard stop solution is added. These temperatures are given for the preferred embodiment of the composite primer consisting of two base-stacked 6-mer oligonucleotides. The reaction occurs at an intermediate temperature, at which the composite primer starts to anneal to the selected annealing site in the template. Here, the phrase "starts to anneal" rather than "anneals" signifies that the reaction may mostly occur above the melting temperature of the composite primer, because at the right conditions it is sufficient for the composite primer to be annealed to the template very briefly to be extended by the polymerase. The amount of water in the beaker determines the cooling rate, which should be sufficiently slow for the particular polymerase being used, to perform the reaction within the required temperature range. One of the differences from the conventional dideoxy sequencing reaction is that the molar amount of the priming oligonucleotide is not recommended to exceed that of the template. Otherwise, at low enough temperature, random binding sites for the priming oligonucleotide all over the template may give rise to primer extension reactions.

The described technique of slowly lowering the temperature can be used for composite primer structures kept together either by base-stacking, or by annealing, or both. If a two step sequencing reaction protocol is used, the temperature lowering procedure is only essential for the initial primer extension. The same is true for the three step protocol, developed recently, in which the third step is a chasing reaction by a thermostable polymerase for removing stoppages caused by secondary structures in high G+C content stretches. The second and the third steps require temperatures optimal for the polymerases involved (e.g. 37° C.–45° C. Sequenase at the second step; and 60° C.–70° C. for thermostable polymerases at the third step). Except the described technique of gradual decrease of temperature, the protocols for the extension reaction of composite primers by various polymerases differ little from the ones for conventional primers, which are well known to those skilled in the art. Generally, lower NaCl concentrations are preferable for composite primer extension reactions, since low NaCl minimizes background priming by the composing oligonucleotides annealed separately from each other.

In contrast to single-stranded DNA template sequencing, double-stranded DNA template has to be denatured. After alkaline-denaturation, the mixture is neutralized by adding 0.1 volumes of 3M sodium acetate (pH 4.5–5.5), and the DNA is precipitated with 2–4 volumes of ethanol and redissolved in distilled water. No separate annealing step is required for double-stranded template. The primer extension/termination reaction components are added to the redissolved template on ice straight after the alkaline-denaturation and precipitation. The reaction is then started in the 40° C. beaker cooling down, as described at the top of this section.

Closed cycle machine for automated sequencing with composite primers:

In yet a further embodiment of the invention, a closed cycle machine using composite primer libraries of manageable size opens prospects for further automation of DNA sequencing. A composite primer library makes it possible to use the same stock of template for recurrent cycles of sequencing without synthesizing a new primer for each cycle. Instead, every round, a "walking" composite primer is composed from the same libraries, as the sequencing advances in the 3' to 5' direction of the template. What makes such libraries feasible for use with automated sequencing machines is that composite primer libraries are about two orders of magnitude smaller than non-composite ones.

Figure 4:
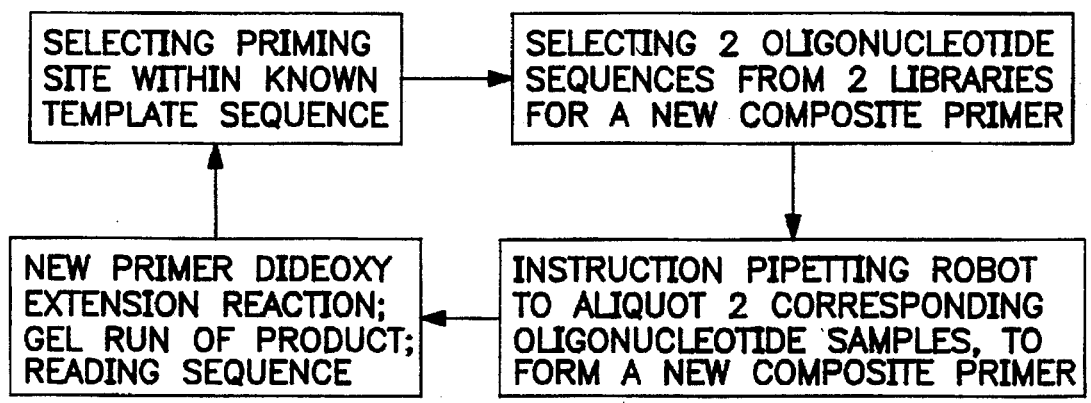
FIG. 4 is a flow chart of work cycle of automated sequencing machine utilizing composite primer libraries.

Automation is already available a) for reading sequence into computer from a running gel with the help of fluorescent band detectors (e.g. ABI, DuPont, Pharmacia, Milligen), b) for loading gels (e.g. Bio-Rad, Calif., USA), and c) for performing the enzymatic chain terminating sequencing reaction by pipetting robots (e.g. Beckman, Calif., USA, and Hitachi, Japan). To complete the sequencing cycle, the composite primer libraries described above and existing pipetting robots can be used for mixing aliquots from the library samples to make a new primer for each cycle. To make this last link of the cycle work, a computer must use the template sequence information obtained in the previous cycle or known otherwise, for a) selecting a priming site within the known portion of the template and b) selecting two composing oligonucleotide sequences from their two libraries to form a composite primer. With this information feedback, the sequencing rounds go on and on along the same template strand as far as the template lasts. FIG. 4 shows a flowchart of the cycle of work of the closed cycle sequencing machine. This method of automated closed cycle sequencing is made possible by the use of composite primers described above. With non-composite primers, such a closed cycle machine does not currently exist, because the large size of non-composite primer libraries makes these libraries (like 8-mer sequences discussed above) impractical to use and even to synthesize. In fact, to the best of my knowledge, such libraries have never been made.

The processive nature of the advance along the same template in the closed cycle sequencing machine achieves more than automation of sequencing per se. It minimizes two much more serious bottle-necks than sequencing per se in present day large scale sequencing projects. These bottle-necks are a) the front end, and b) the back end. The front end is the preparation of the template, including subcloning and the preceding steps. Presently, the preparation has to be done for each run, except in the walking primer strategy, which is not too often used in current large scale sequencing projects, because of the high cost of and the time delay by the primer synthesis. The back end is the integration of the sequences obtained from individual runs, and is at present considered the worst bottle-neck in large scale sequencing.

Description of the closed cycle machine for sequencing with composite primers:

Except for the composite primer libraries described earlier, most other material components and blocks of components of the closed cycle sequencing system can be essentially similar to those in the machines used today. They are known to persons skilled in the art. Nevertheless, I would like to mention a few technical details here. For the described cyclic mode of work, the gels have to be either reusable or automatically changeable. Either possibility can be realized in the closed cycle sequencing machine. I prefer an electrophoresis system of reusable capillary gels (e.g. Cohen, A. et al. 1990 J. of Chromatography 516, pp. 49–60) for several reasons: 1) Their reusability has been well established. 2) Capillary gels are loaded by electrophoretic injection, and thus allow a relatively easy automation of loading. 3) Fluorescent detectors of electrophoretic bands are much more sensitive for capillary gels than for slab gels. 4) Capillary gels allow very high electric field and thus much faster runs than slab gels, thanks to their low heat dissipation. This is especially useful in closed cycle sequencing with composite primers, where other time consuming steps, like primer synthesis or template preparation, are minimized or eliminated.

A preferred embodiment of the closed cycle sequencing system comprises a pipetting robot, like Biomek workstation (Beckman Instruments, California, USA), for performing dideoxy sequencing reaction. The automatic workstation is programmed to aliquot appropriate samples from oligonucleotide libraries described above for the composite primer, whose structure can comprise two or more composing oligonucleotides. The libraries are stored in 0.5 ml tubes and are located within the range of the pipetting mechanism of the robot. The sequencing reactions are prepared and performed automatically in the standard way robots like Biomek operate.

The electrophoresis is performed in capillaries (fused-silica tubing from Polymicro Technologies, Arizona, USA) of 0.075 mm inner diameter and up to 100 cm long, filled with 6% polyacrylamide gel, 8M urea and 50 mM TBE. During the electrophoresis run, the cathodic end (the loading end) of each capillary is immersed in a buffer chamber with 50 mM TBE, 8M urea and the negative electrode. The anodic end (exit end) of each capillary is immersed in a similar buffer chamber with the positive electrode. Power supplies of up to 60 kV d.c. are available from Glassman, N.J., USA.

For loading the DNA samples, the loading end of the capillary is lifted from the electrophoretic buffer of negative electrode by a stepping motor mechanism, and together with the negative electrode is dipped into the sequencing reaction products denatured by heating in 80% formamide. The standard electrophoretic injection of DNA into the gel is then performed by turning the voltage of about 100 V/cm on. The injection takes 10–30 sec, the voltage is turned off, the loading end of the capillary is returned into the buffer chamber of the negative electrode, the voltage of about 300 V/cm is turned on, and the run begins. The entire work cycle of the closed cycle machine is controlled by computer commands.

The detection of the electrophoretic bands of the DNA is performed by a fluorescence detector monitoring a narrow window in the capillary near the exit end. The standard detector comprises a 25 mW Omnichrome argon ion laser (air cooled) tuned to 488 nm excitation wavelength (for Fluorescein as fluorophor); and a Hamamatsu PMT tube as a sensor. All priming oligonucleotides carry the same fluorescent label of FITC (Fluorescein). The fluorescent label is excited by the laser at 488 nm, focused on the detection window of the capillary. The emission signal is detected by the PMT (Photo Multiplier Tube) after a focusing lens and a cut off filter. The signal is transmitted to an A/D interface (Nelson Analytical, California, USA) for transfer to the computer. For reading the sequence, signals from at least 4 different capillaries have to be compared by the computer.

Here arises a problem commonly encountered in sequencing machines. (Most of these machines are currently using slab gels, but this problem can arise in capillary electrophoresis as well.) In different capillaries (or lanes in slab gels), DNA fragments of the same size reach the detection window at slightly different time due to small variations in capillary length, electric field, gel conditions and other parameters. Our solution to this problem is to run more than one dideoxy terminator in one capillary. For example, the first capillary is loaded with A+C (reactions terminated by ddATP and by ddCTP terminators). The second capillary is loaded with C+G. The third: with G+T, the fourth: with T+A, the fifth: with A+G, and the sixth: with C+T. These six capillaries exhaust all possible combinations of any 2 out of the 4 terminators. The computer makes a slight time-shift in the signal from each capillary to align (synchronize) properly all six outputs. The criterion for the correct value of the time-shift is the right correlation of the signals. For example, A+C and C+G signals should have the same C-bands (should overlap at the C-bands), C+G and A+G signals should have the same G-bands, and A+C and A+G signals should have the same A-bands. If the bands in different signals originating from the same type of terminator are correctly aligned and matched, then the three overlaps of signals mentioned above, C-bands, G-bands, and A-bands, should reconstitute the A+C, C+G, and G+A signals, when added pair-wise. This reconstitution represents a criterion for correct time shift value introduced. Therefore, optimizing the time-shifts is a relatively straighforward task for the computer. The synchronization of the signals is further facilitated by the fact that the beginning of the sequence (near the primer) is usually known. Each shift can be ramped as a function of time, and the ramp does not have to be linear, but can preferably use the first two or three polynomial powers. This method of synchronizing the signals from different capillaries is also useful for aligning signals from different lanes in slab gels. The use of six rather than four capillaries for reading one sequence gives a redundancy of information so helpful for automatically resolving difficult sequence reading problems. Such redundancy may not help, if a problem of compression is encountered. Then the computer has options to repeat the reaction with dITP or 7-deaza-2'-dGTP instead of dGTP in order to rerun and reread the difficult sequence, or/and to run a gel with formamide.

Except for the novel way to optimize the time shift, described in the preceding paragraph, the software for reading DNA sequence from electrophoretic band pattern is well developed. Most available software packages, can be used in the closed cycle sequencing machine, and a skilled programmer can write a new program for sequence reading. In practice, most people automating sequence reading prefer writing their own software. With the signal alignment problem of the preceding paragraph solved, and with no smiling or tilting of bands in capillary electrophoresis, such programming is quite straightforward.

After the sequence is read, the computer software selects an annealing site for composite primer within the newly read sequence for the next cycle of sequencing. In computerized selection of the annealing site, as in manual one, annealing sites involved in stable secondary structures, like hairpins, are advised to avoid. A variety of software is available for secondary structure assessment.

Within the selected annealing site, the computer specifies a priming binding site and an auxiliary binding site for annealing of the composing oligonucleotides. After specifying the two binding sites in the template sequence, the computer software selects two sequences of composing oligonucleotides from their libraries to form a composite primer discussed above. In accordance with the structure of the composite primer, these oligonucleotides should comprise sequences complementary to the selected binding sites. The computer then instructs the pipetting robot to aliquot samples of the selected oligonucleotides and to perform the sequencing reaction in order to continue with the next sequencing cycle, as shown in FIG. 4.

Composite probes:

In yet another aspect of the present invention, a combination of two or more oligonucleotides can serve as a composite probe. The concept of a composite probe is similar to that of a composite primer. In fact, a composite probe can be constructed not only in the same way, but often from the same oligonucleotides and from the same libraries as a composite primer held together by annealing between the composing oligonucleotides (as in FIG. 2). The main difference is that the probe is used mainly for nucleic acid detection rather than for primer extension reaction.

Like the composite primer described above, a composite probe comprises two or more oligonucleotides, which are selected to bind chosen binding sites on the target DNA strand close enough to one another for the composing oligonucleotides to be in contact with each other while annealed to these binding sites. The contact can be annealing of complementary segments of the composing oligonucleotides. The contact by annealing keeps the oligonucleotides together and enhances their affinity to the target strand, as compared to the affinity of either of them alone. The mechanism of enhancement of the affinity of composite probe is similar to "Reason 1" for superior priming efficiency of composite primers discussed above. The greater the probe-to-target annealing length, the more unique the probe is. The composite probe, therefore, possesses a much enhanced sequence specificity of binding to the target DNA strand, as compared to either of the composing oligonucleotides used alone.

For the purpose of detection, the probe should have either radioactive, or chemiluminescent, or fluorescent, or some other detectable label. Such a label can be attached directly to an oligonucleotide sample from one of the composite primer libraries. To do that, one can extend the 3'-end of one of the composing oligonucleotides by a terminal transferase with dNTP carrying one of the labels mentioned above. For radioactive labeling, one can also attach a radioactive phosphate to the 5'-end by phosphorylation. Alternatively, a labeled (for example, biotinylated) oligonucleotide library can be synthesized specifically for composite probes.

Clarifications:

The term "binding site" for an oligonucleotide on a template strand does not imply that this binding site has to be complementary to the entire oligonucleotide like in some base-stacked composite primers shown above. The binding site can be only complementary to a part of the oligonucleotide, like, for example, in the composite primer formed by annealing between composing oligonucleotides.

In both Figures and text, prefix "d" denoting deoxy is often omitted, when DNA sequences and individual nucleotides are listed.

Generally, each sample in an oligonucleotide library contains oligonucleotides of the same sequence. However, occasionally, one or more positions within the oligonucleotide may be degenerate.

For the purpose of the claims, an oligonucleotide library is termed complete, if it comprises all possible sequences of the oligonucleotide segment, which anneals to the template or target DNA, excluding degenerate base positions.

For the purpose of the claims, the term "channel of electrophoresis" refers to channels like lanes in slab gel electrophoresis or capillaries in capillary gel electrophoresis.

Although the description above contains many specificities, these should not be construed as limiting the scope of the invention, but as merely providing illustrations of some of the presently preferred embodiments of the invention. For example, the composite primer can be composed of a different number of oligonucleotides, which can have different sequences, and can be linked (or be in contact) within the composite primer by different types of links. The invention should not be limited to DNA and should include the possibility of one or both strands of the above description being RNA strands, as well as the nucleic acid polymerases being not only DNA but also RNA polymerases. Nor is the usage of composite primers limited to sequencing. For example, composite primer extension reaction can be used to produce probes (radioactively or otherwise labeled, or unlabeled) complementary to single-stranded nucleic acids, either DNA or RNA. Another example is measurement of the distance between the end-labeled 5'-end of the priming oligonucleotide and the 5'-terminus of RNA, which serves as a template. (The labeled products of this primer extension reaction are run in denaturing polyacrylamide gel electrophoresis.) The method of analysis of lengths of extended DNA fragments does not have to be limited to gel electrophoresis. The analysis can be done for example, by mass spectrometry. Thus the scope of the invention is determined by the appended claims and their legal equivalents, rather than by the examples given.

What is claimed is:

1. A method for sequence specific priming of an extension reaction comprising;
    a) annealing two or more covalently unconnected oligonucleotides to a template to form a composite primer, wherein at least two of said oligonucleotides comprise mutually complementary sequences and each oligonucleotide comprises a sequence complementary to a sequence in said template; and two or more of said oligonucleotides anneal to adjacent sites on the template and to each other thereby increasing the sequence specificity of priming as compared to the sequence specificity of priming by one of said oligonucleotides alone; and
    b) extending the composite primer with a nucleic acid polymerase.

2. The method of claim 1 wherein one or more of said oligonucleotides comprise a modified 3'-terminus that prevents enzymatic extension of said 3'-terminus.

3. The method of claim 1 wherein one of said oligonucleotides is covalently linked to a chemical selected from the group consisting of a radioisotope, an amino group, a carboxy group, a biotin molecule and a fluorescent molecule.

4. The method of claim 1 wherein at least one of said oligonucleotides contains a modified nucleotide.

5. A method for priming an extension reaction comprising the steps of:
    a) annealing a priming oligonucleotide to the nucleic acid;
    b) annealing a first auxiliary oligonucleotide to the nucleic acid adjacent to said priming oligonucleotide wherein said priming oligonucleotide and said first auxiliary oligonucleotide comprise mutually complementary sequences that anneal with each other forming a composite primer; and c) extending the composite primer with a polymerase using the nucleic acid as a template.

6. The method of claim 5 wherein the portion of the priming oligonucleotide or the auxiliary oligonucleotide annealed to the nucleic acid is between about 3 to about 12 nucleotides in length.

7. The method of claim 5 wherein the portion of the priming oligonucleotide or the auxiliary oligonucleotide annealed to the nucleic acid contains at least one base position that is degenerate.

8. The method of claim 5 wherein said auxiliary oligonucleotide has a modified 3'-terminus that inhibits extension from said 3'-terminus.

9. The method of claim 5 wherein the composite primer is labeled.

10. The method of claim 9 wherein the label is selected from a group which consists of a radioisotope, a fluorescent marker, a biotin molecule, and a chemiluminescent terminus.

11. The method of claim 5 further comprising the step of annealing another oligonucleotide to the nucleic acid adjacent to said priming oligonucleotide wherein said another oligonucleotide and said priming oligonucleotide are not annealed to each other.

12. The method of claim 5 further comprising the step of annealing a second auxiliary oligonucleotide to the nucleic acid adjacent to said auxiliary oligonucleotide wherein said second auxiliary oligonucleotide and said auxiliary oligonucleotide are annealed to each other.

13. The method of claim 5 wherein at least one of said oligonucleotides contains a modified nucleotide.

\* \* \* \* \*